US010092755B1

(12) United States Patent
Andresen et al.

(10) Patent No.: US 10,092,755 B1
(45) Date of Patent: Oct. 9, 2018

(54) NEURAL STIMULATOR PLACEMENT

(71) Applicant: Micron Devices LLC, Miami Beach, FL (US)

(72) Inventors: Chad David Andresen, Miami Beach, FL (US); Laura Tyler Perryman, Miami Beach, FL (US)

(73) Assignee: Micro Devices LLC, Pompano Beach, FL (US)

( * ) Notice: Subject to any disclaimer, the term of this patent is extended or adjusted under 35 U.S.C. 154(b) by 0 days.

(21) Appl. No.: 15/064,739

(22) Filed: Mar. 9, 2016

Related U.S. Application Data

(60) Provisional application No. 62/130,477, filed on Mar. 9, 2015.

(51) Int. Cl.
*A61N 1/36* (2006.01)
*A61N 1/05* (2006.01)
*A61N 1/372* (2006.01)

(52) U.S. Cl.
CPC ....... *A61N 1/36096* (2013.01); *A61N 1/0551* (2013.01); *A61N 1/36053* (2013.01); *A61N 1/37205* (2013.01); *A61N 1/36114* (2013.01)

(58) Field of Classification Search
CPC .. A61N 1/36053; A61N 1/36096; A61N 1/40; A61N 1/36114; A61N 1/0551; A61N 1/37205
See application file for complete search history.

(56) References Cited

U.S. PATENT DOCUMENTS

2005/0065575 A1* 3/2005 Dobak .............. A61N 1/36007
607/45
2009/0275996 A1* 11/2009 Burnes ................ A61N 1/0558
607/2

FOREIGN PATENT DOCUMENTS

| WO | WO 2012/103519 | 8/2012 |
| WO | WO 2012/138782 | 2/2013 |
| WO | WO 2013/019757 | 2/2013 |
| WO | WO 2013/025632 | 2/2013 |
| WO | WO 2013/040549 | 3/2013 |

* cited by examiner

*Primary Examiner* — Howie Matthews
(74) *Attorney, Agent, or Firm* — Fish & Richardson P.C.

(57) ABSTRACT

A method for implanting a wireless neural stimulator device, the method including: inserting a device through a patient's skin on a lateral side of a patient's neck, wherein the device includes with a proximal end, a distal end, a first opening at the proximal end, a second opening at the distal end, and a lumen extending between the first opening and the second opening; after inserting the device through the patient's skin, advancing the distal end towards a perivascular bundle of the patient until the distal end is proximate to the perivascular bundle; inserting the wireless neural stimulator device through the first opening; and advancing the wireless neural stimulator from the first opening through the lumen until the wireless neural stimulator exits the second opening and is proximate to the vagus nerve such that the neural stimulator is able to stimulate the vagus nerve.

7 Claims, 15 Drawing Sheets

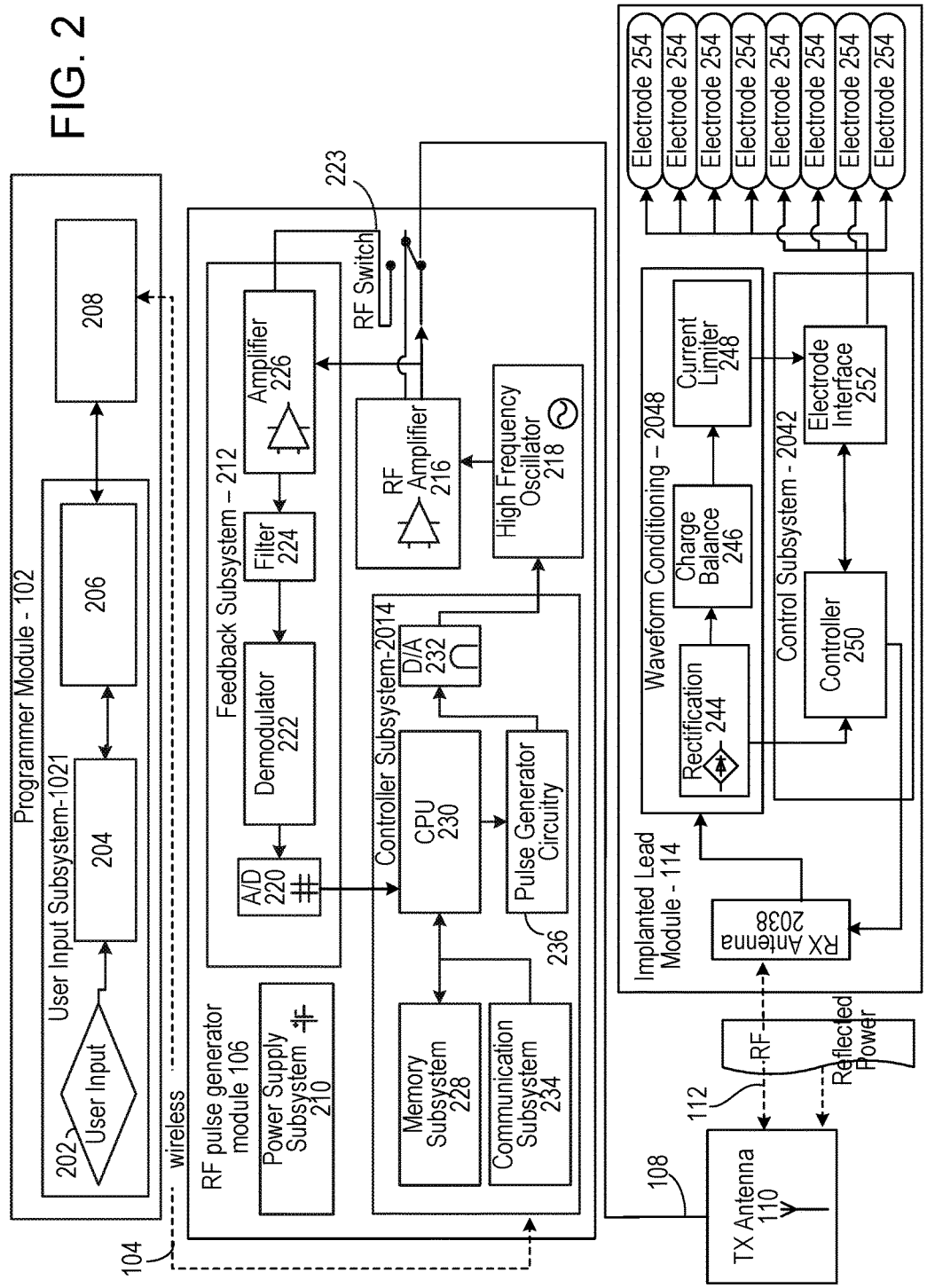

NEURAL STIMULATOR PLACEMENT

CROSS-REFERENCE TO RELATED APPLICATION

This application claims the benefit of U.S. Provisional Application No. 62/130,477, filed Mar. 9, 2015, and titled "Neural Stimulator Placement," which is incorporated by reference.

TECHNICAL FIELD

This application relates to procedures for implanting neural stimulators at or in the vicinity of the vagus nerve for stimulation.

BACKGROUND

Pharmaceutical depression treatment can result in a resistance to medication within a few years, leading to a diagnosis of treatment resistant major depression (TRMD). A variety of therapeutic intra-body electrical stimulation techniques can treat chronic disabling conditions such as TRMD. For instance, devices may be used to deliver stimulatory signals for vagus nerve stimulation (VNS), which can provide anti-depression benefit.

SUMMARY

Some implementations provide a method for implanting a wireless neural stimulator device. The method includes inserting a device through a patient's skin on a lateral side of a patient's neck, wherein the device includes with a proximal end, a distal end, a first opening at the proximal end, a second opening at the distal end, and a lumen extending between the first opening and the second opening; after inserting the device through the patient's skin, advancing the distal end towards a perivascular bundle of the patient until the distal end is proximate to the perivascular bundle; inserting the wireless neural stimulator device through the first opening; and advancing the wireless neural stimulator from the first opening through the lumen until the wireless neural stimulator exits the second opening and is proximate to the vagus nerve such that the neural stimulator is able to stimulate the vagus nerve.

Implementations may include one or more of the following features.

The device may be an introducer. Inserting the device through the patient's skin may include inserting an assembly of a needle stylet and the introducer through the patient's skin; and advancing the distal end of the device towards the perivascular bundle comprises advancing a distal end of the assembly of the needle stylet and introducer towards the perivascular bundle.

The method may include: before inserting the wireless neural stimulator device through the first opening, removing the needle stylet from the assembly of the needle stylet and introducer.

The device may be an introducer. The method may include: inserting a needle through the patient's skin on the lateral side of the patient's neck; advancing the needle toward the perivascular bundle until a distal end of the needle is proximate the perivascular bundle; passing a guide wire through the needle until a distal end of the guide wire passes out of an opening at the distal end of the needle; removing the needle; and wherein advancing the distal end of the introducer towards a perivascular bundle of the patient until the distal end is proximate to the perivascular bundle comprises passing the introducer along the guide wire until the distal end of the introducer is proximate to the perivascular bundle.

The method may include: prior to inserting the wireless neural stimulator device through the first opening, removing the guide wire.

The wireless neural stimulator device may be implanted without implanting an implantable pulse generator (IPG) in the patient's body. The wireless neural stimulator device may be implanted without running a wire to connect the wireless neural stimulator to an external power source.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 2 depicts a detailed diagram of an example of the wireless stimulation system.

Like reference symbols in the various drawings indicate like elements.

DETAILED DESCRIPTION

In various implementations, systems and methods are disclosed for applying one or more electrical impulses to targeted excitable tissue, such as nerves, for treating of the complications of epilepsy, inflammation, arthritis, sleep apnea, seizures, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

The wireless implantable stimulator device disclosed herein may be implanted for vagus nerve stimulation (VNS) to provide symptom relief to patients with various modalities. Such implantation is generally performed at the neck region. More details of the implantation can be found in FIGS. 3A-4H and the discussions thereof.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

Figure 1:
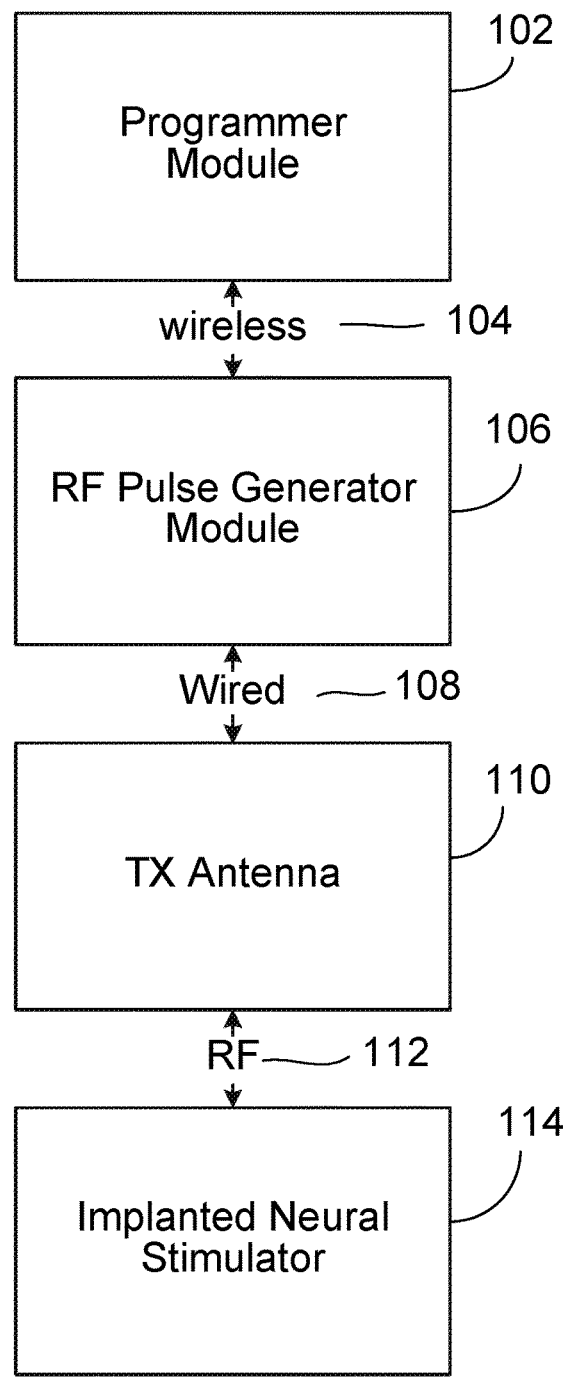
FIG. 1 depicts a high-level diagram of an example of a wireless stimulation system.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
|---|---|
| Pulse Amplitude: | 0 to 20 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Some methods include implantation of a wireless neural stimulator device to treat disorders that can be therapeutically influenced by vagus nerve stimulation (VNS). Such conditions include neurological disorders. Examples include refractory depression, anxiety disorders, Alzheimer's disease, Parkinson's disease, epilepsy, migraines, fibromyalgia, obesity, and tinnitus. For context, vagus nerve stimulation (VNS) is believed to modulate mood and seizure control, for example, through alteration of norepinephrine release. The norepinephrine release may be altered by projections of solitary tract to the locus coeruleus, elevated levels of inhibitory gamma-Aminobutyric acid (GABA) related to vagal stimulation and inhibition of aberrant cortical activity by reticular activation system. The treatable conditions include inflammation disorders such as arthritis, hypertension, etc.

In some implementations, electrodes may be implanted near the vagus nerve in the neck region in-between a jugular vein and a carotid artery. These methods include placement of wireless neural stimulation devices, for example, under ultrasound guidance, and may be performed as part of an outpatient procedure and may only use local anesthesia. The implanted wireless stimulator device does not include a power supply, such as a battery, and is powered remotely by, for example, electromagnetic energy radiated from a microwave field stimulator (MFS). The lack of an independent power source on the implanted wireless stimulator may enable a compact form factor, which is highly conducive to implantation in a crowded space, such as the neck region to target the vagus nerve. Moreover, such peripheral nerve implantations may not necessitate the withholding of anti-platelet therapy and anticoagulants, something typically administered to senior citizens who are more likely to suffer a particular neurological disorder than younger people. Below, examples of peripheral implantation are described in the context of vagus nerve stimulation.

Figure 3A:
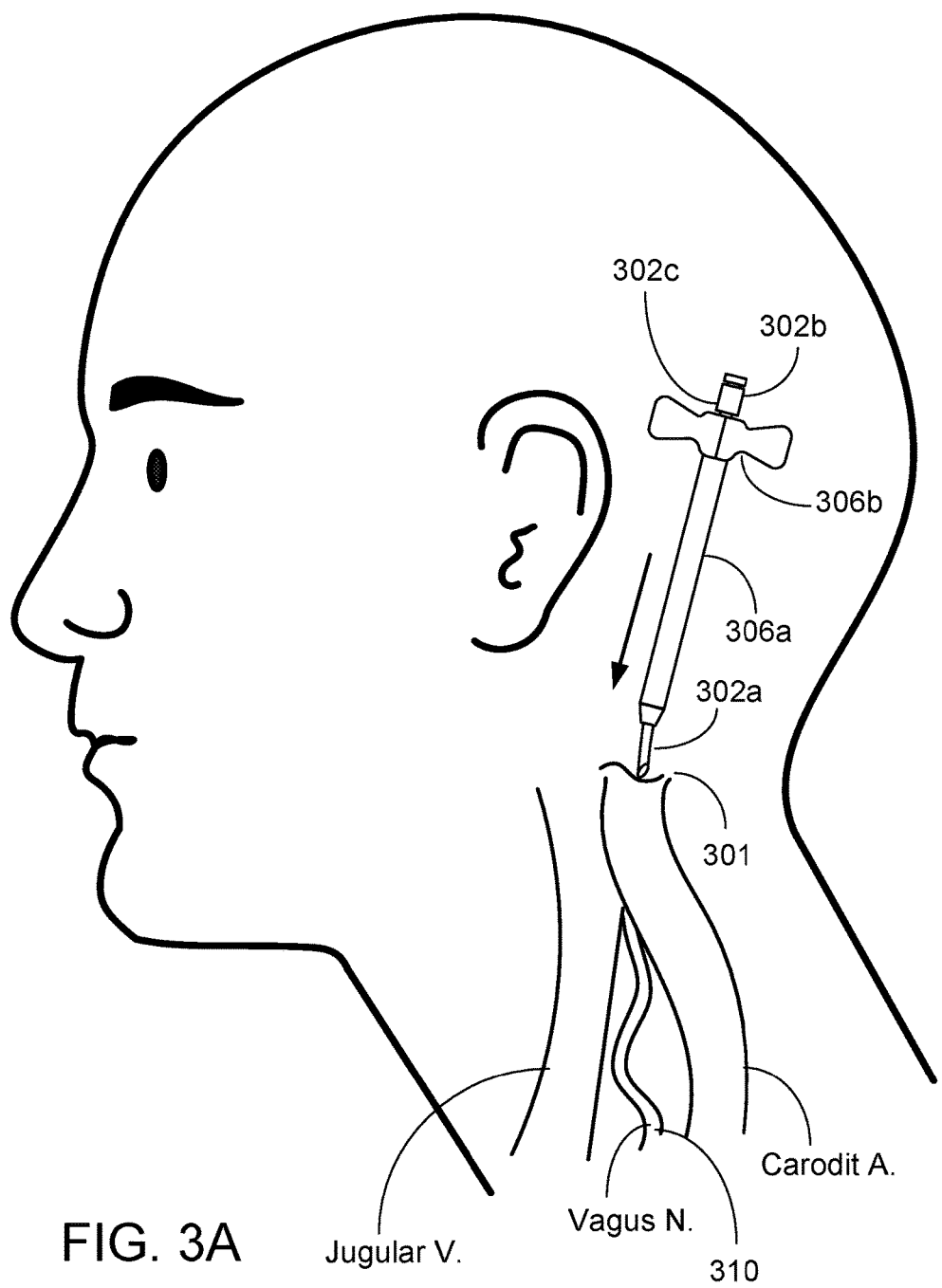
FIGS. 3A-3D illustrate an example of implanting a wireless neural stimulator device for vagus nerve stimulation.

FIGS. 3A-3D illustrate an example of implanting a wireless neural stimulator device 308 for VNS. As illustrated in FIG. 3A, initially, a treating physician marks an entry point 301 on the lateral neck for accessing the vagus nerve percutaneously. For instance, the entry point 301 may generally be on the skin of the location on the left lateral neck and over the carotid artery. Next, an introducer 306, along with a needle stylet 302, are inserted through the skin at entry point 301 and advanced inferiorly towards the perivascular bundle where the common carotid, the jugular vein, and the vagus nerve (VN) overlap. To provide a backdrop of soft tissue surroundings for the insertion process, the treating physician can use ultrasound guidance, the same guidance process as used in the Seldinger technique. In an example, the insertion angle, as defined by the angle formed between the longitudinal axis of the needle stylet 302 and the skin surface of the patient, may be approximately 20 to 30 degrees. Introducer 306 has an elongated, generally tubular sheath section 306a and a handle section 306b. The sheath section 306a may be of gauge 13 or smaller and includes a pair of weakened sections (not illustrated) that extend longitudinally along the sheath 306a and are located opposite one another on the sheath 306a. The handle section 306b includes handle members 306c and 306d that meet at split portion 306e. The split portion 306e is aligned with the weakened sections of the sheath section 306a. The introducer 306 may also be referred to as an introducer cannula. The introducer 306 includes an inner lumen that extends longitudinally from an opening at the handle section 306b, through the handle section 306b and sheath section 306a, to an opening at the end of the sheath section 306a. Needle stylet 302 generally fits in the inner lumen of the introducer 306 and can be inserted into and withdrawn therefrom. The needle stylet 302 is generally tubular and includes a proximal end 302a and a distal end 302b. The proximal end of the needle stylet 302 includes a stop portion 302c and the distal end 302b includes a beveled portion 302d to facilitate movement of the introducer 306 and stylet 302 through the layer of the tissue. The beveled portion 302d includes an opening. Needle stylet 302 also has its own inner lumen that extends from an opening at the proximal end 302a to the opening of the beveled portion 302d at the distal end 302b. As shown, the needle stylet 302 can be placed into and advanced through the inner lumen of the introducer 306 until the stop portion 302c engages the handle section 306b and the beveled portion 302d extends beyond the sheath section 306a. In this configuration, the introducer 306, along with the needle stylet 302 are inserted through entry point 301 and advanced inferiorly towards the space between the left common carotid and the left jugular vein until the introducer 306 and needle stylet 302 are firmly placed within the tissue and the distal mouth of the introducer is anterior of the intended stimulation site, e.g., vagus nerve 310. During the insertion process, the needle stylet 302 and introducer 306 are made of a material and dull tip as to not be capable of penetrating through the carotid sheath or the jugular vein sheath. The devices are advanced through the tissue under ultrasound guidance. Both introducer 306 and needle stylet 302 may be made of polyurethane, silicone, polytetrafluoroethylene (PTFE), or rubber.

Figure 3B:
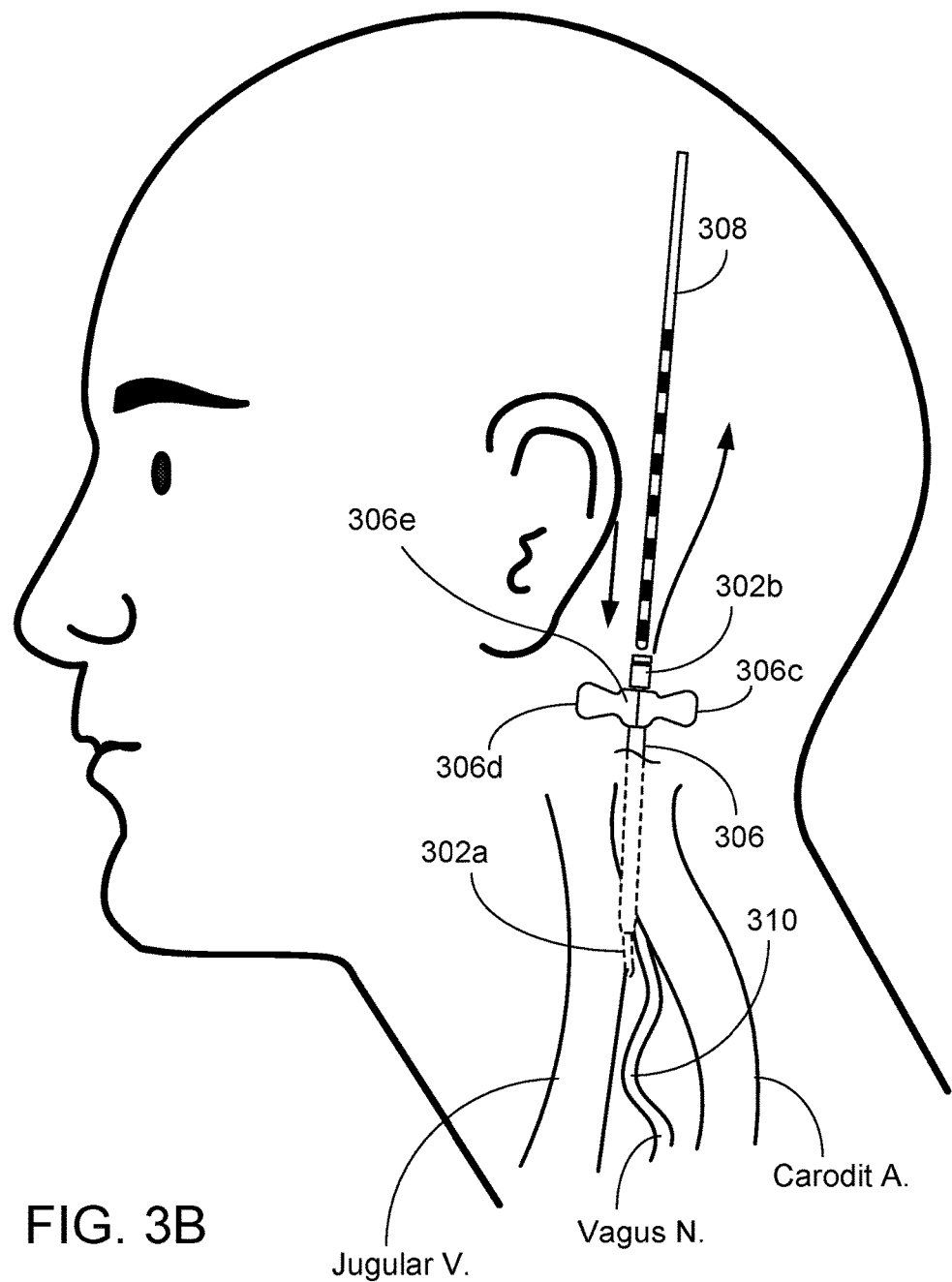
Figure 3C:
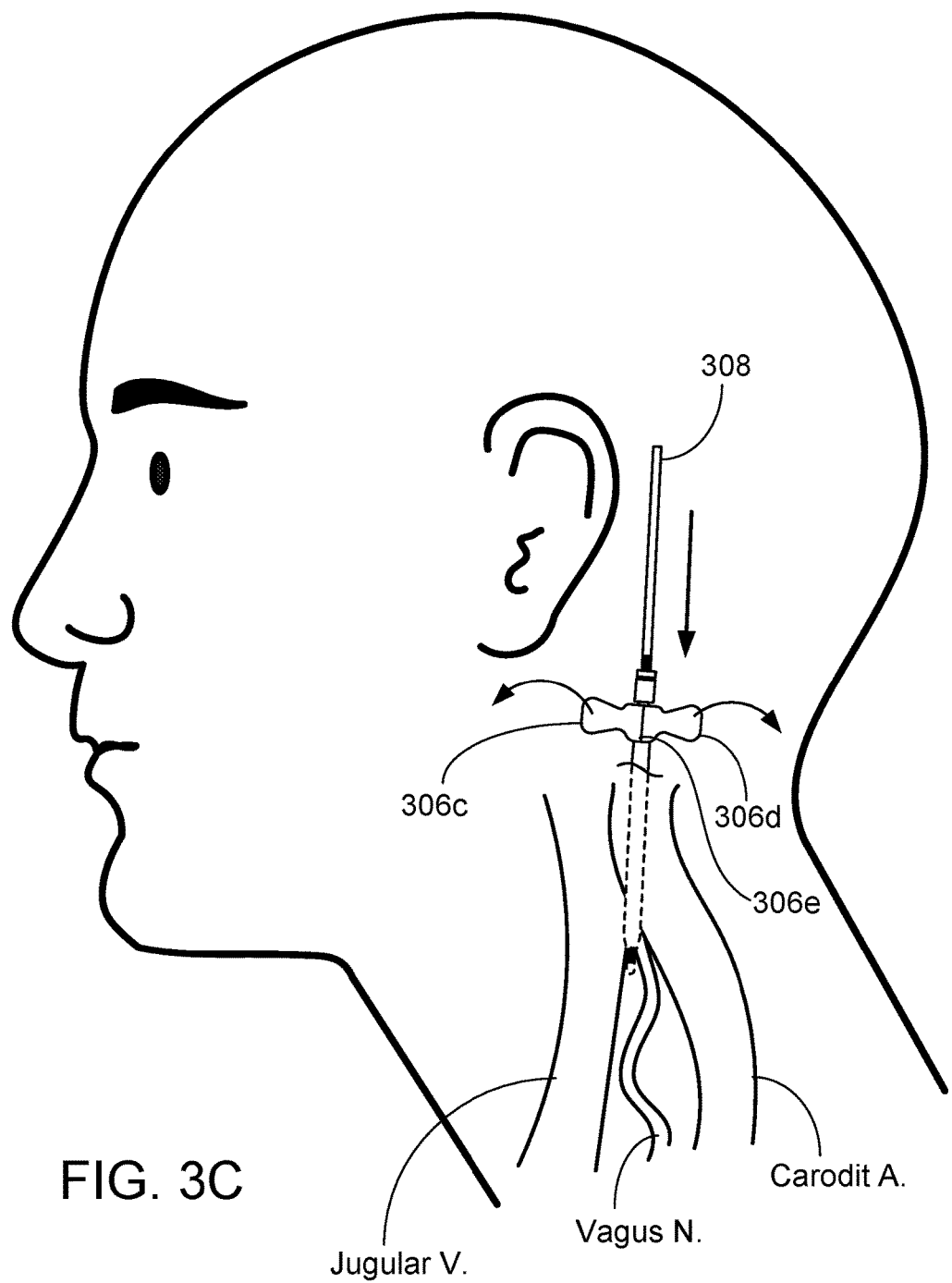

Referring to FIGS. 3B-3C, once the distal mouth of the introducer 306 and needle stylet 302 are situated near the target site, for example, the vagus nerve between the space between the left jugular vein and left common carotid artery, the needle stylet 302 is removed. Then a wireless neural stimulator device 308 is inserted through the opening, located at the proximal end of introducer 306, to the inner lumen of the introducer 306 and advanced through the inner lumen until the tip 308a of the wireless neural stimulator device 308 passes through the opening of the beveled portion 302d into the tissue space between the left jugular vein and left common carotid artery such that the distal portion of the device 308 is proximate the vagus nerve. For example, the physician may advance the wireless neural stimulator device 308 through the inner lumen until substantial resistance is met as a result of the tip 308a passing through the opening of the beveled portion 302d and contacting tissue. In some instances, the physician may use ultrasound sonography to guide the tip of the wireless neural stimulator device 308 as it exits the opening of the beveled portion 302. The stimulator device 308 is powered and tested to validate its proper placement relative to the vagus nerve such that the stimulator device 308 is able to stimulate the vagus nerve. The soft tissue surroundings in the neck region may facilitate ultrasound sonography guidance. For context, the wireless neural stimulator device 308 is shaped and sized with the form factor to fit in the inner lumen of introducer 306. A portion of an example of the wireless neural stimulator device 308 is shown and described below in FIG. 3E. Inserting wireless neural stimulator device 308 into the neck space may not require fluoroscopic guidance while the insertion of a wireless neural stimulator device into an epidural space may involve monitoring the insertion by, for example, X-ray fluoroscopy. This difference is partly due to the difference in implantation depth and tissue surroundings.

Thereafter, as illustrated in FIG. 3C, the introducer 306 is withdrawn. In this example, handle members 306c and 306d of introducer are pulled apart as illustrated by the arrows, which results in the split portion 306e splitting apart. The physician continues pulling apart the handle members 306c and 306d, which splits the sheath section 306a along the weakened sections, while also pulling the handles members 306c and 306d laterally away from entry point 301, which results in the sheath portion 306e being pulled out of entry point 301 so that only the device 308 remains.

Figure 3D:
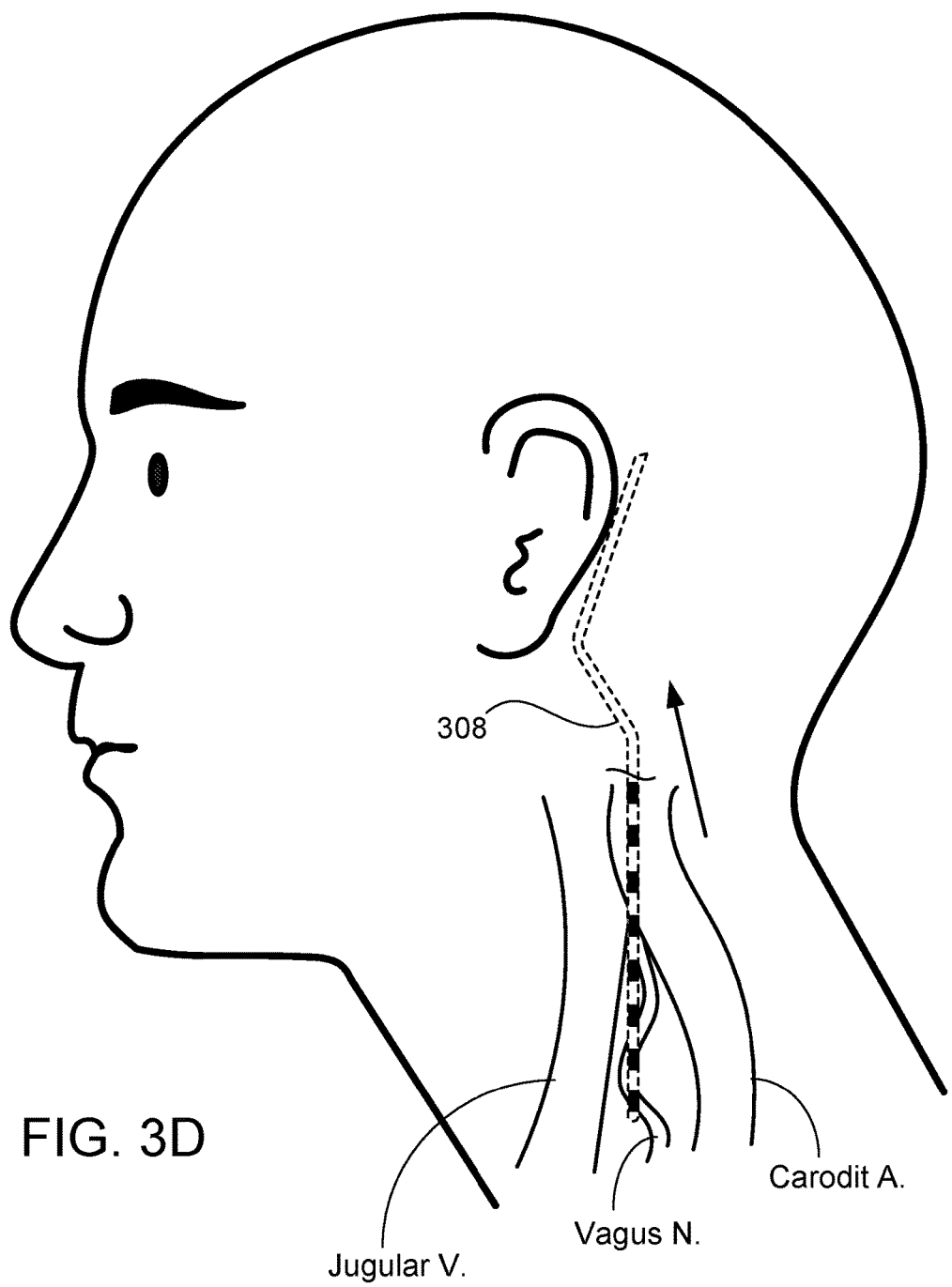

Referring to FIG. 3D, after the introducer 306 has been removed, wireless neural stimulator device 308 may be anchored. For example, in some instances, neural stimulator device 308, implanted on the lateral side of the left neck, may be partially positioned over the left ear, for example, with its proximal tail routed cranially and behind the left ear, albeit without suture. The tail of neural stimulator device 308 can be placed under the skin and the distal end of the neural stimulator device 308 with the electrodes is placed towards the target area. In other cases, any excess portion of the device 308 that is extending outside of tissue entry point 301 may be trimmed, and the wireless neural stimulator device 308 may be anchored or sutured to the surrounding tissue near entry point 301. To suture the neural stimulator device 308, the physician may run the suture stitch directly through its soft plastic body or loop suture around the stimulator device 308 itself noninvasively.

Figure 3E:
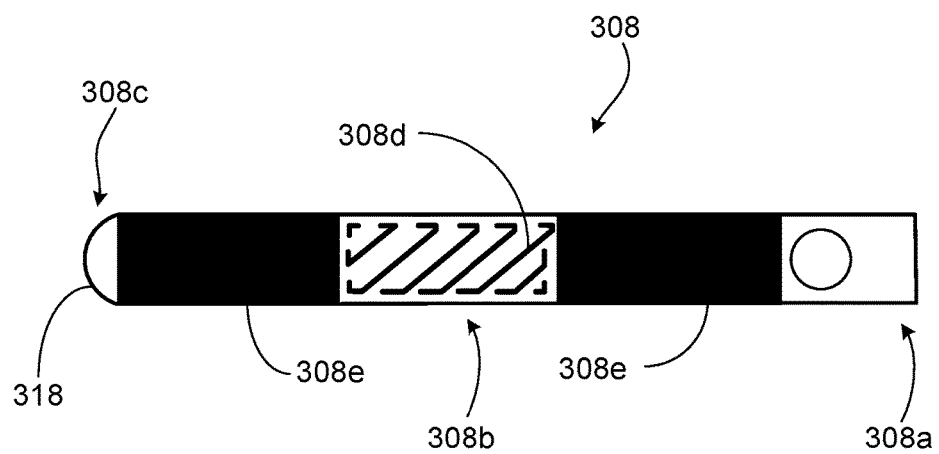
FIG. 3E illustrates an example of a wireless neural stimulator device.

FIG. 3E shows an example of a distal portion of a wireless neural stimulator device 308 that includes a non-conductive distal end 308a, and device body 308b. Distal end 308a may have a rounded tip 318 with a smooth finish to allow for navigating through tissue. Wireless neural stimulator device 308 may also include cylindrically shaped electrodes 306e spaced at, for example, between 0.25 mm and 6.0 mm. Wireless neural stimulator device 308 may also include a soft plastic body that houses electronic circuitry 306d. Wireless neural stimulator device 308 may be implemented as described above, for example, with respect to any of FIGS. 1-2.

Figure 4A:
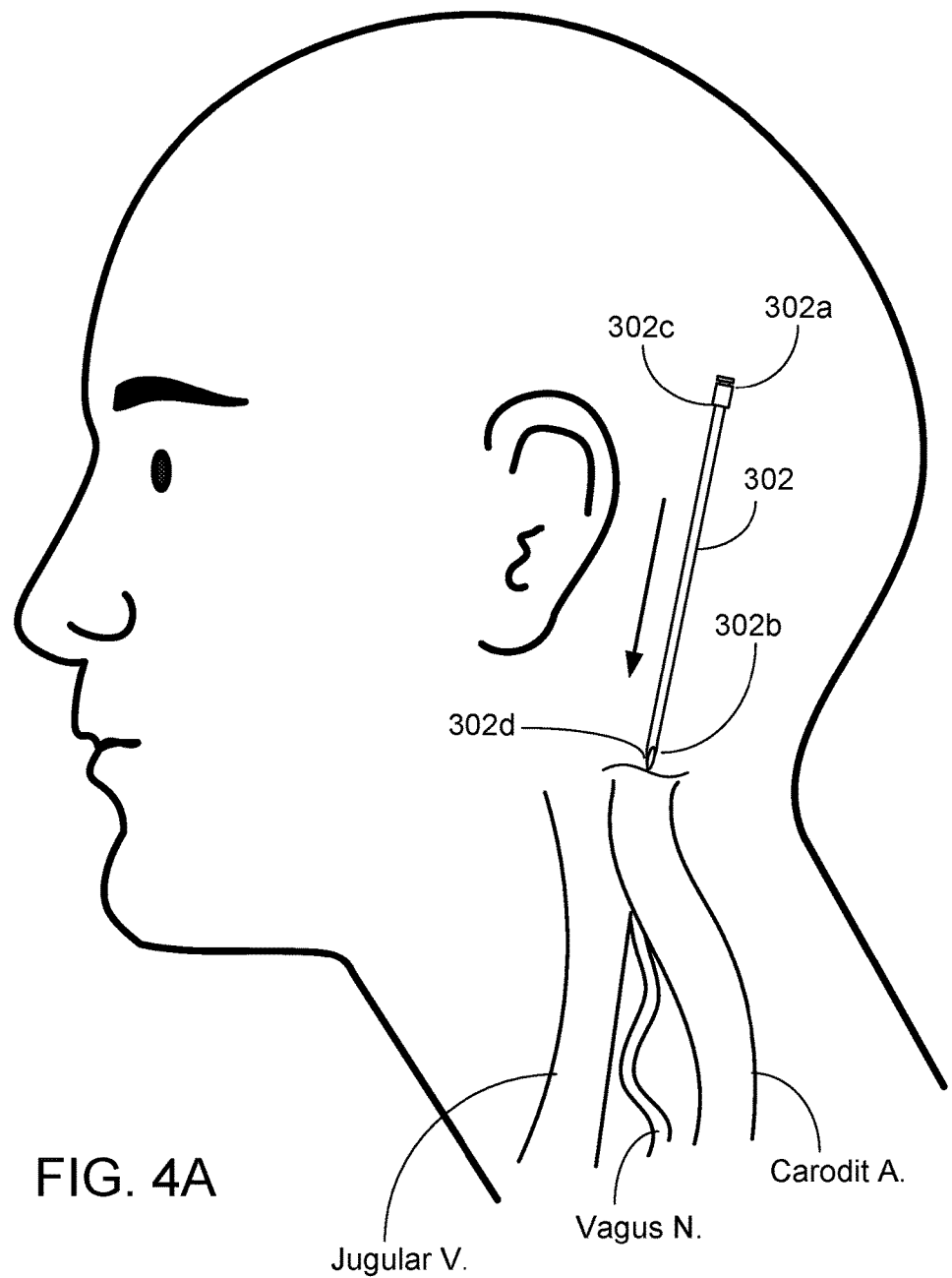
FIGS. 4A-4H illustrate another example of implanting a wireless neural stimulator device for vagus nerve stimulation.

FIGS. 4A-4H illustrate another example of implanting a wireless neural stimulator device 308 for vagus nerve stimulation (VNS). This example highlights the use of a technique similar to the Seldinger technique to access the vagus nerve from the neck area percutaneously under ultrasound guidance. Initially, as illustrated in FIG. 4A, needle 402 is inserted through the skin, for example, at a marked entry point 401, on the lateral neck. Needle 402 is generally tubular with a hollow inner lumen. Needle 402 includes a proximal end 402a and a distal tip 402b. The proximal tip 402a includes a stop portion 402c and the distal tip 402b includes a beveled end 402d that has an opening. The hollow inner lumen extends from the opening at the proximal tip 402a to the opening of the beveled portion 402d at the distal tip 402b. In some instances, needle 402 is a 20-gauge needle made of metal, such as stainless steel.

Figure 4B:
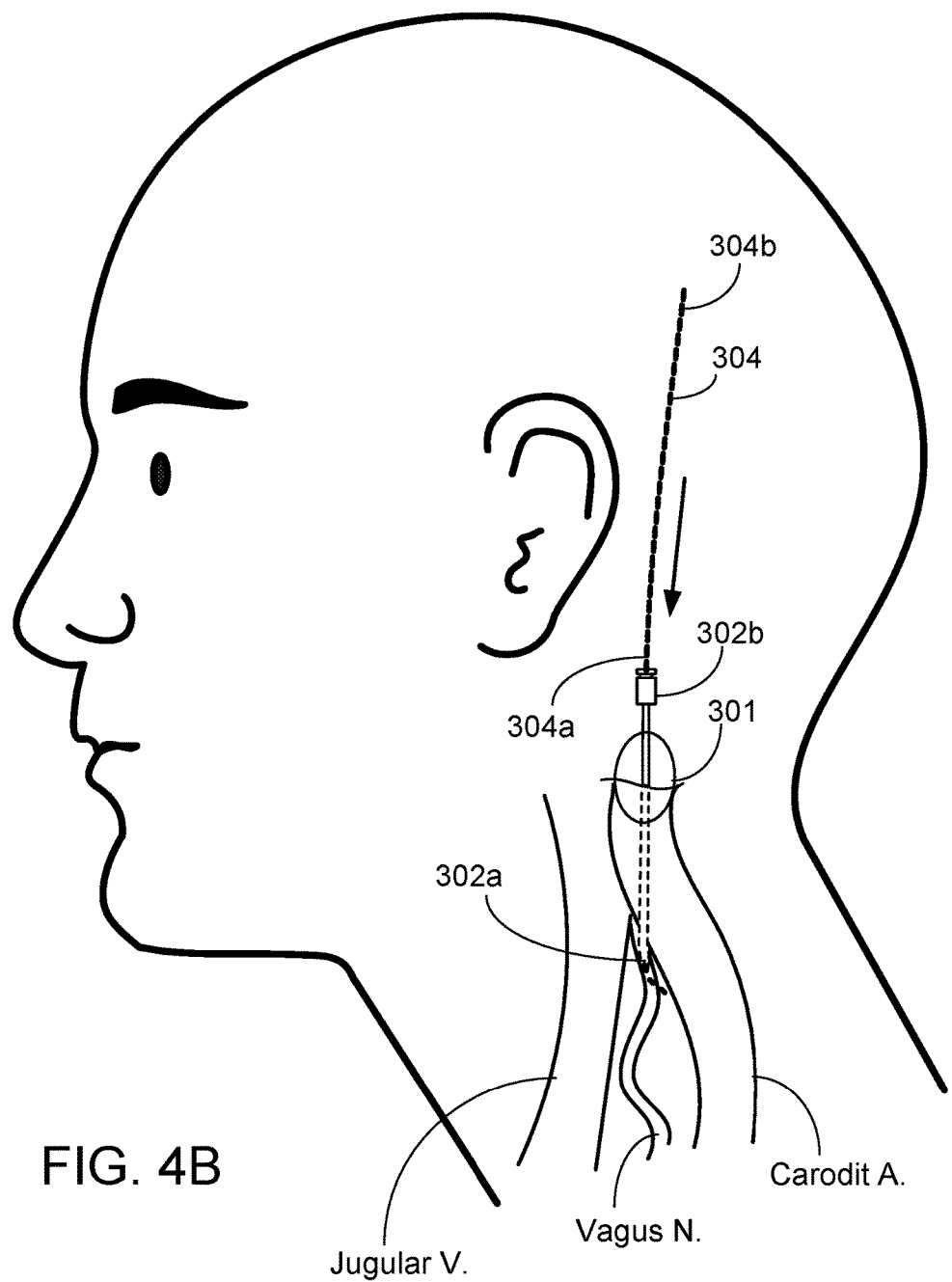
Figure 4C:
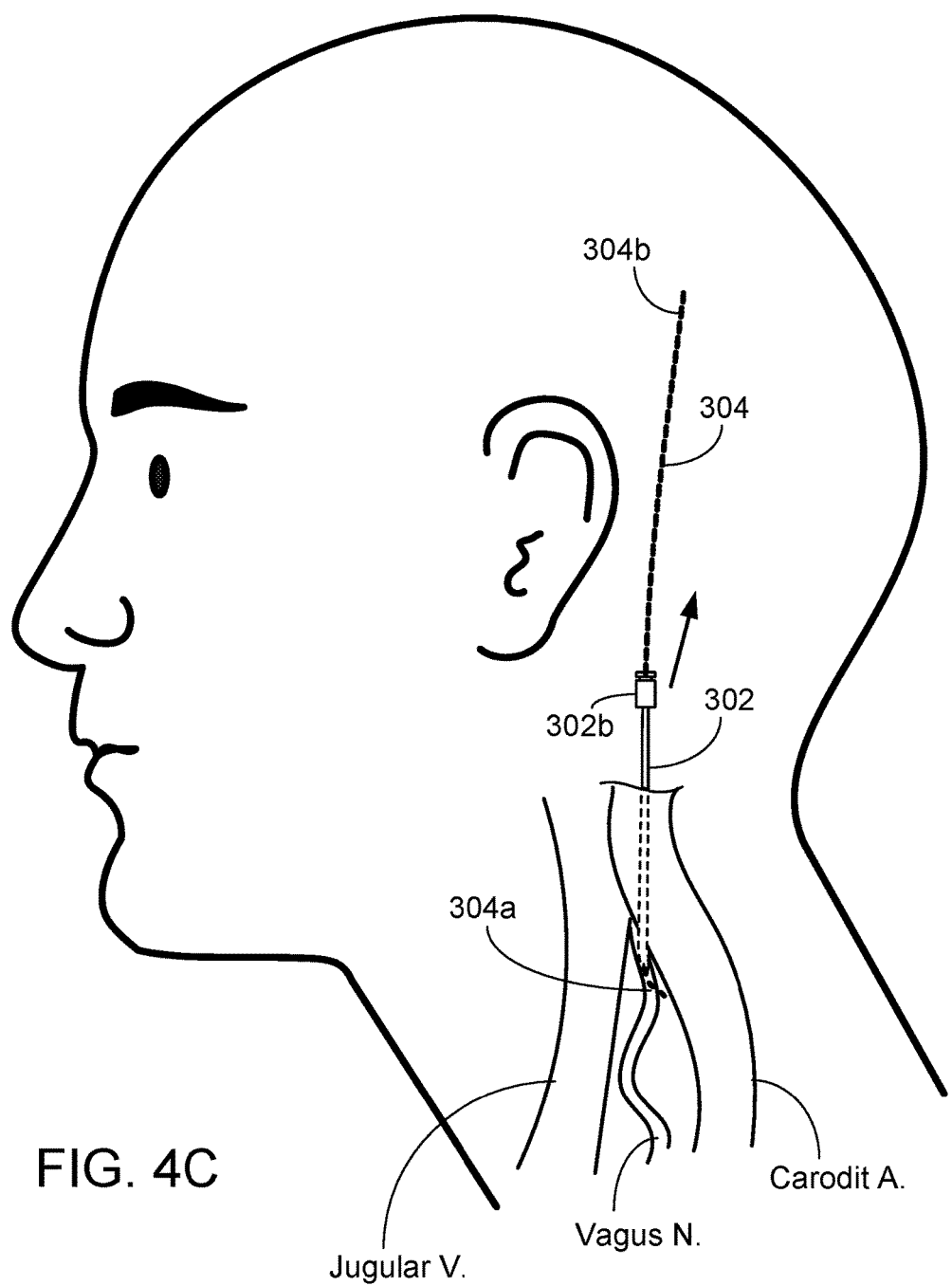

As illustrated in FIG. 4B, needle 402 is advanced so that the distal tip 402b is superior but proximate the perivascular bundle between the common carotid artery and the jugular vein under ultrasound guidance. Once needle 402 is in place, guide wire 404 is inserted through the inner lumen of needle 402. Guide wire 404 may be made of metal, be generally flexible, and have a rounded tip. Guide wire 404 may be stranded to reinforce the strength of the guide wire. Guide wire 404 includes a proximal end 404b and a distal end 404a. In some instances, ultrasound guidance provides an overview of the soft tissue surroundings and guide wire 404 is inserted through the inner lumen of needle 402 such that the distal end 404a passes through the distal tip 402b of the needle 402 and approaches the intended perivascular bundle. Once guide wire 404 is positioned, needle 402 can be removed, as illustrated in FIG. 4C.

Figure 4D:
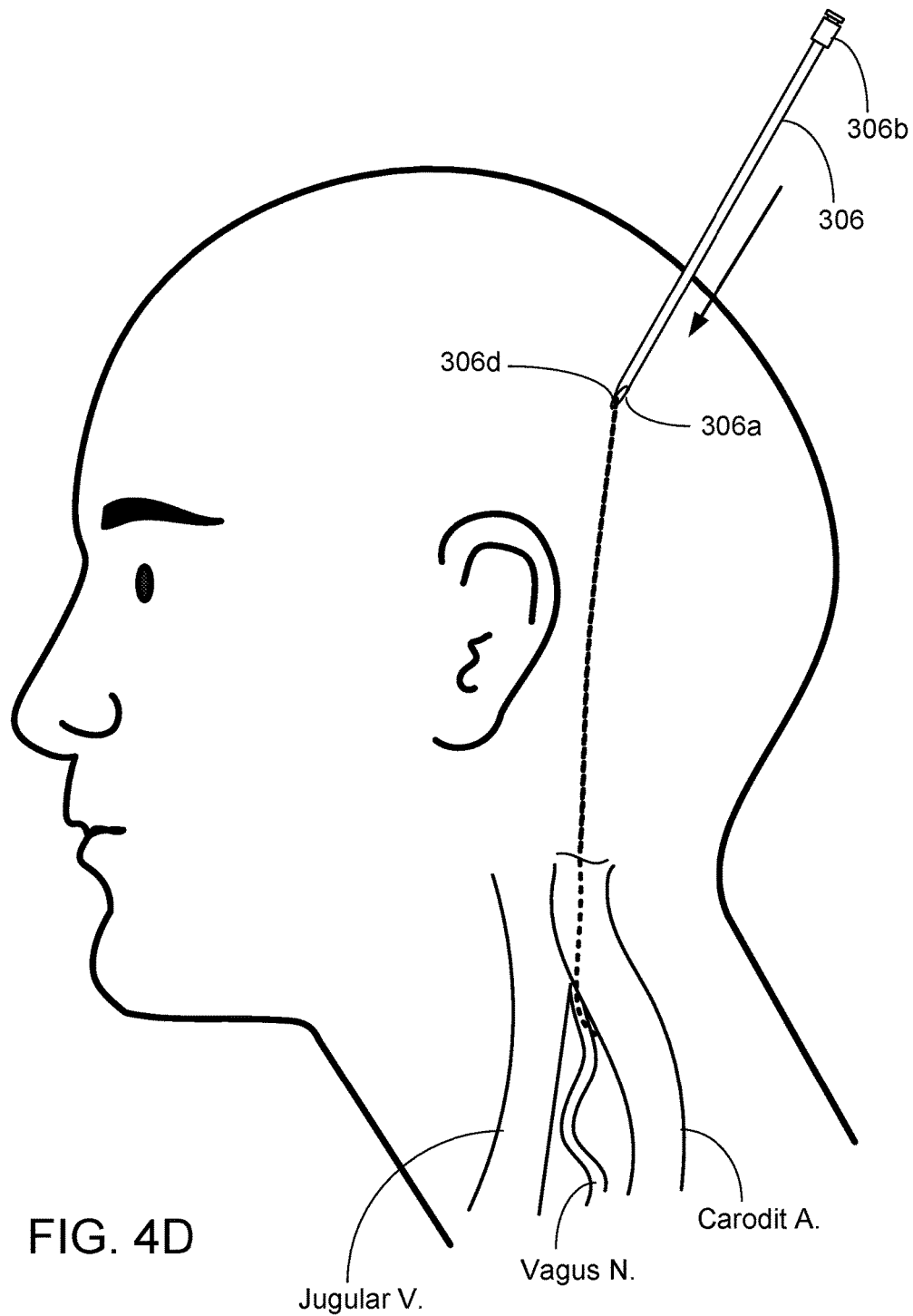
Figure 4E:
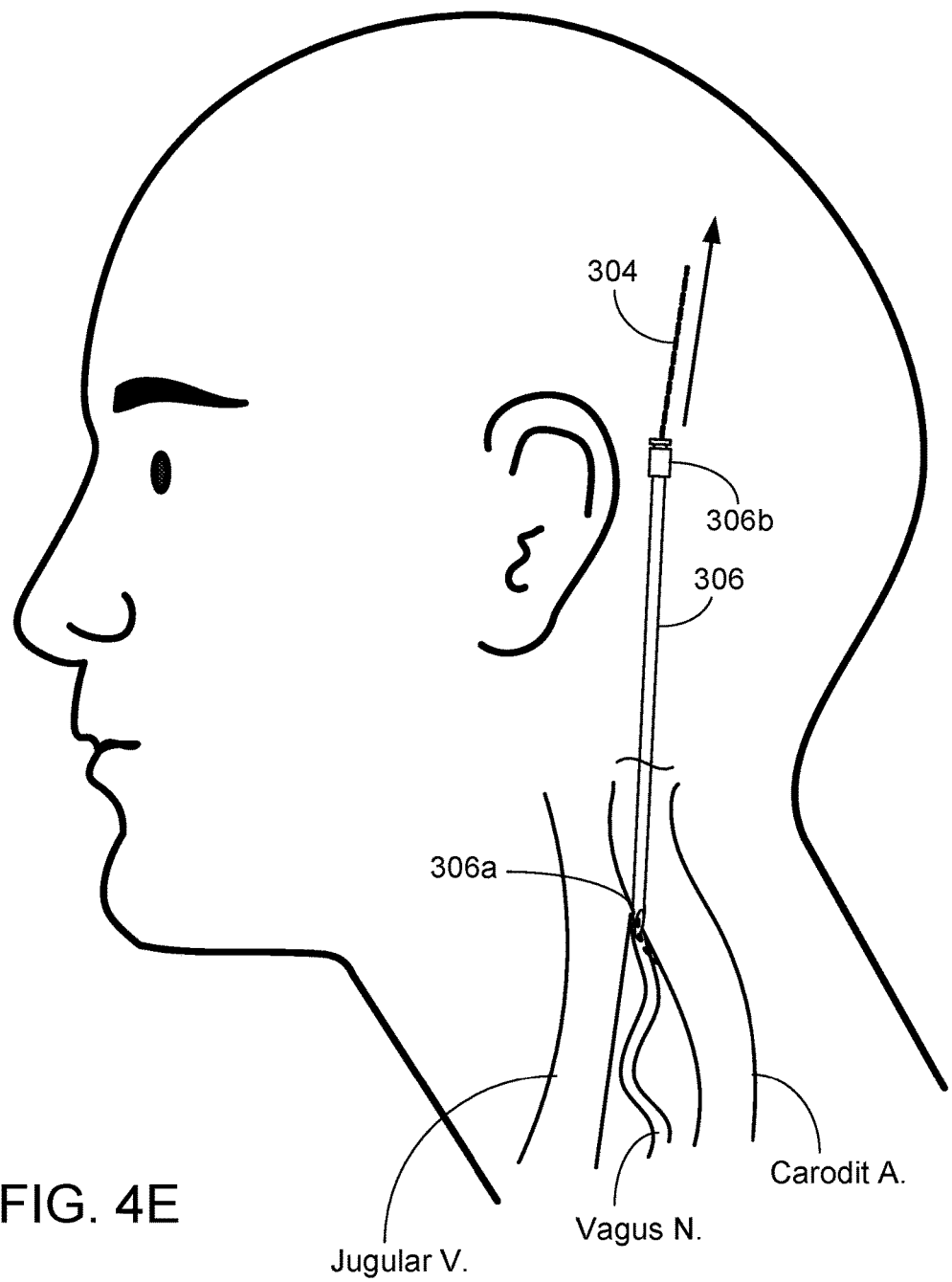

Subsequently, introducer 406 is mounted on the proximal end 404b of the guide wire and then passed along guide wire 404, as illustrated in FIGS. 4D-E, under ultrasound guidance. Introducer 406 may also be referred to as an introducer cannula. Introducer 406 includes an inner lumen that extends longitudinally from an opening at the handle section 406b, through the handle section 406b and sheath section 406a, to an opening at the distal end 406d of the sheath section 1506a. In some instances, introducer 406 may be a 15-gauge introducer. Introducer 406 is positioned with the distal end 406d near the perivascular bundle. Thereafter, the treating physician may hold the introducer 406 in place while removing guide wire 404 from the inner lumen of introducer 406.

Figure 4F:
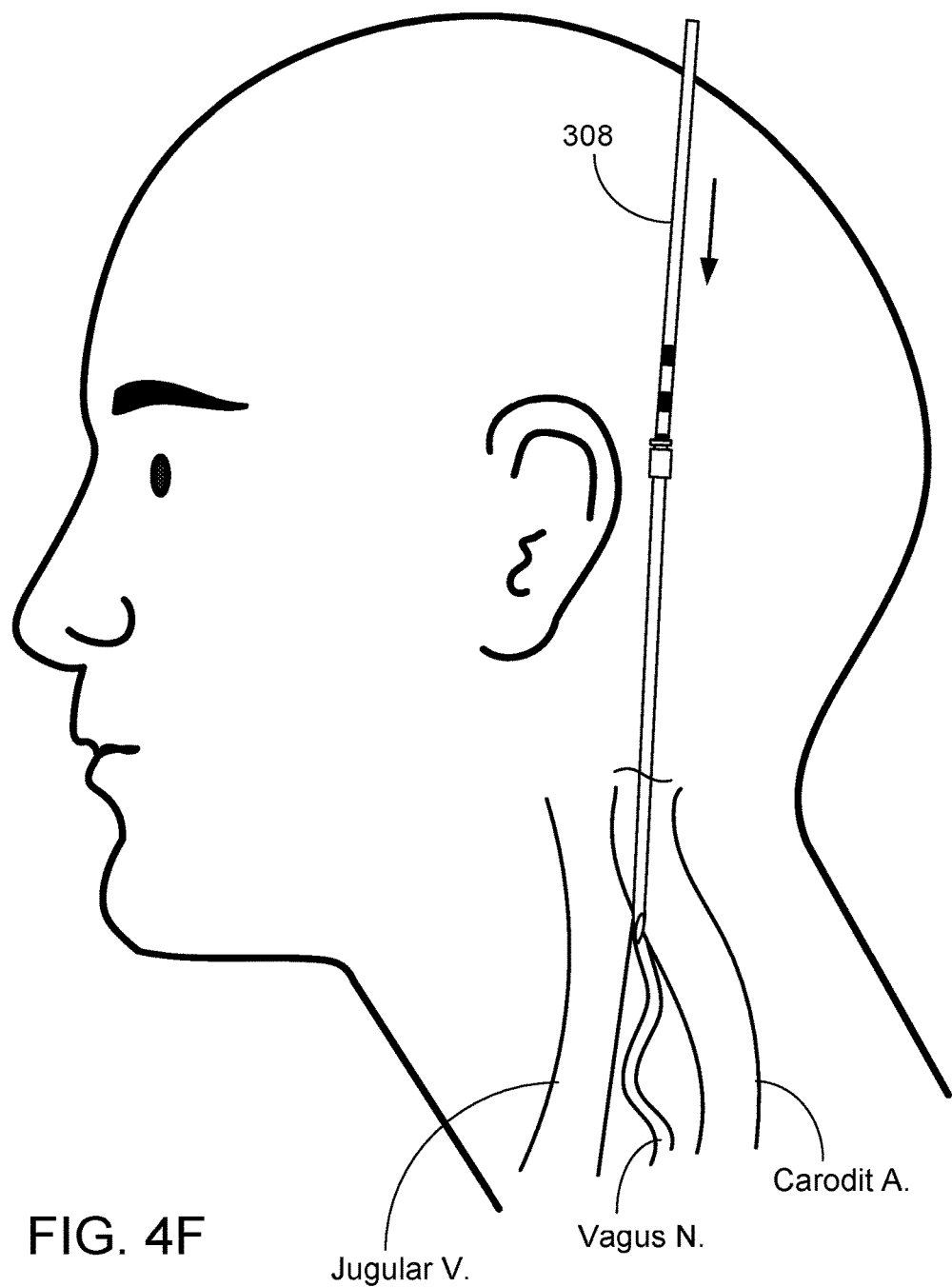
Figure 4G:
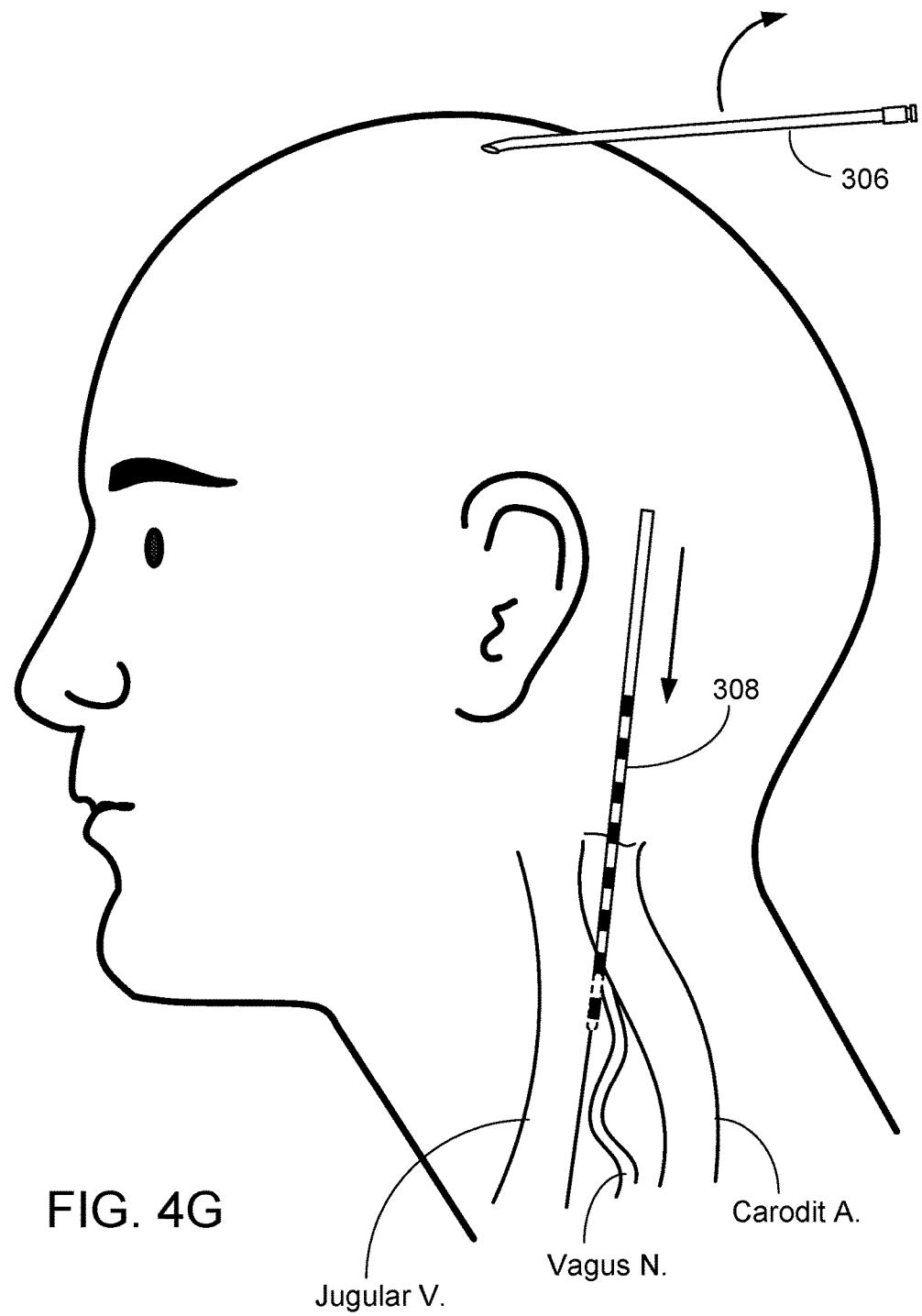
Figure 4H:
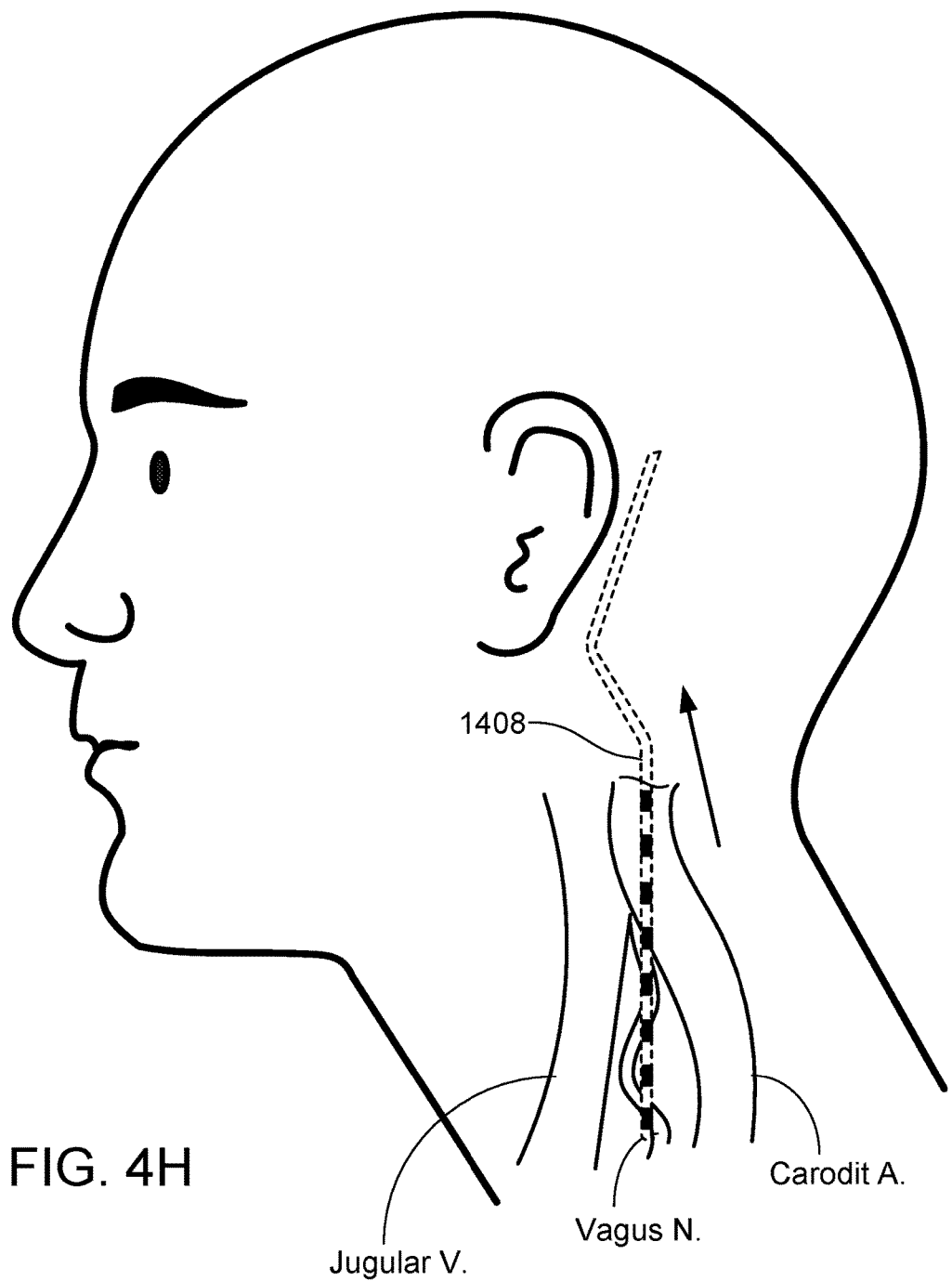

Referring to FIGS. 4F-4G, once the guide wire 404 has been removed from the inner lumen of introducer 406, wireless stimulator device 308 is inserted into the inner lumen of introducer 406 and advanced through the inner lumen. The wireless neural stimulator device 308 is advanced until the distal portion of the device 308 passes through the opening at the distal end of the sheath 406a and enters into the tissue space between the left jugular vein and left common carotid artery such that the distal portion of the device 308 is proximate the vagus nerve. The insertion generally follows a superior-inferior axis and is guided by ultrasound sonography. Once the wireless neural stimulator device 308 is in place such that the device is able to stimulate the vagus nerve, introducer 406 may be withdrawn by pulling the introducer 406 away while holding the wireless neural stimulator device 308 in place. For context, a portion of an example of a wireless neural stimulator device 308 has been described above with regard to FIG. 3E.

When the introducer 406 is taken off of the wireless neural stimulator device 308, the tail end of wireless neural stimulator device 308 may be placed near the left ear, for example, with its tail end routed cranially and behind the left ear, albeit without suture. The tail of neural stimulator device 308 is placed under the skin with the distal portion of the neural stimulator device 308 placed towards the target stimulation area. In other cases, any excess portion of the device 308 extending outside of entry point 301 may be trimmed, and the wireless neural stimulator device 308 may be anchored or sutured to the surrounding tissue near entry point 301. To suture the neural stimulator device 308, the physician may run the suture stitch directly through its soft plastic body or loop suture around the stimulator device 308 itself noninvasively.

A number of implementations have been described. Nevertheless, it will be understood that various modifications may be made. Accordingly, other implementations are within the scope of the following claims.

What is claimed is:

1. A method for implanting a wireless neural stimulator device, the method comprising:
percutaneously inserting a introducer device through a patient's skin on a lateral side of a patient's neck, wherein the device includes a proximal end, a distal end, a first opening at the proximal end, a second opening at the distal end, and a lumen extending between the first opening and the second opening;
after inserting the introducer device through the patient's skin, advancing the distal end of the introducer device towards a perivascular bundle of the patient until the distal end is proximate to the perivascular bundle;
inserting the wireless neural stimulator device through the first opening at the proximal end of the introducer device; and
advancing the wireless neural stimulator from the first opening through the lumen of the introducer device until the wireless neural stimulator exits the second opening at the distal end of the introducer device and becomes proximate to the vagus nerve such that the wireless neural stimulator is implanted to stimulate the vagus nerve by non-inductively receiving, via one or more dipole antennas on the wireless neural stimulator device, an input signal;

creating one or more electrical pulses solely using electrical energy contained in the received input signal, and applying the created one or more electrical pulses to simulate the vagus nerve.

2. The method of claim 1, wherein:

inserting the device through the patient's skin comprises inserting an assembly of a needle stylet and the introducer device through the patient's skin; and advancing the distal end of the introducer device towards the perivascular bundle comprises advancing a distal end of the assembly of the needle stylet and introducer device towards the perivascular bundle.

3. The method of claim 2 further comprising, before inserting the wireless neural stimulator device through the first opening at the proximal end of the introducer device, removing the needle stylet from the assembly of the needle stylet and introducer device.

4. The method of claim 1, further comprising:

inserting a needle through the patient's skin on the lateral side of the patient's neck;

advancing the needle toward the perivascular bundle until a distal end of the needle is proximate the perivascular bundle;

passing a guide wire through the needle until a distal end of the guide wire passes out of an opening at the distal end of the needle;

removing the needle; and wherein advancing the distal end of the introducer device towards a perivascular bundle of the patient until the distal end is proximate to the perivascular bundle comprises passing the introducer device along the guide wire until the distal end of the introducer device is proximate to the perivascular bundle.

5. The method of claim 4 further comprising, prior to inserting the wireless neural stimulator device through the first opening at the proximal end of the introducer device, removing the guide wire.

6. The method of claim 1, wherein the wireless neural stimulator device is implanted without implanting an implantable pulse generator (IPG) in the patient's body.

7. The method of claim 1, wherein the wireless neural stimulator device is implanted without running a wire to connect the wireless neural stimulator to an external power source.

* * * * *

UNITED STATES PATENT AND TRADEMARK OFFICE
CERTIFICATE OF CORRECTION

| | | |
|---|---|---|
| PATENT NO. | : 10,092,755 B1 | Page 1 of 1 |
| APPLICATION NO. | : 15/064739 | |
| DATED | : October 9, 2018 | |
| INVENTOR(S) | : Chad David Andresen and Laura Tyler Perryman | |

It is certified that error appears in the above-identified patent and that said Letters Patent is hereby corrected as shown below:

On the Title Page

Column 1 (Assignee), delete "Micro" and insert -- Micron --, therefor.

In the Claims

In Claim 4, Column 18, Line 2, after "proximate" delete "the" and insert -- to --.

Signed and Sealed this
Fifth Day of February, 2019

Andrei Iancu
*Director of the United States Patent and Trademark Office*